United States Patent
Harada et al.

(10) Patent No.: US 6,173,600 B1
(45) Date of Patent: *Jan. 16, 2001

(54) MEASURING INSTRUMENT WITH MEMORY

(75) Inventors: Yasuyuki Harada; Jiro Murayama; Yasushi Haketa; Tetsuya Sato; Eiji Kato; Akihiko Kato, all of Saitama-ken (JP)

(73) Assignee: TAO Electronics Ltd., Tokyo (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/224,773

(22) Filed: Jan. 4, 1999

(30) Foreign Application Priority Data

Oct. 7, 1998 (JP) .................................................. 10-285765

(51) Int. Cl.[7] .................................................. G01L 27/00

(52) U.S. Cl. .................................................. 73/1.06

(58) Field of Search .................................... 73/1.02, 1.03, 73/1.06; 374/1, 3; 324/438; 422/82.04

(56) References Cited

U.S. PATENT DOCUMENTS

| | | | |
|---|---|---|---|
| 4,223,549 | * | 9/1980 | Kitzinger ............................. 73/1.02 |
| 4,260,950 | * | 4/1981 | Hadden et al. ....................... 73/1.02 |
| 4,481,804 | * | 11/1984 | Eberhard et al. ..................... 73/1.06 |
| 5,022,980 | * | 6/1991 | Tanaka et al. ......................... 73/1.02 |
| 5,124,659 | * | 6/1992 | Frola et al. ............................ 73/1.02 |

* cited by examiner

*Primary Examiner*—Robert Raevis
(74) *Attorney, Agent, or Firm*—Akin, Gump, Strauss, Hauer & Feld, L.L.P.

(57) ABSTRACT

According to the present invention, there is provided a measuring instrument with a memory or measuring electrodes each having a memory, which does not require setting of a calibration or correction value at each replacement of the electrode, permits automatic recognition of information such as the model name or the manufacture No. of the electrode in the instrument body, and allows free selection of an appropriate electrode for each use. The measuring instrument 1 has an instrument body 20 and a measuring electrode 10 releasably connected to the instrument body 20. Storage means 15 for storing information regarding the measuring electrode 10 in the measuring electrode 10, or in a cable 12 or a connector 13 for connecting the measuring electrode 10 to the instrument body 20.

10 Claims, 10 Drawing Sheets

MEASURING INSTRUMENT WITH MEMORY

BACKGROUND OF THE INVENTION

The present invention relates to a measuring instrument such as a pH meter, an ion meter or a conductivity meter, provided with measuring electrodes which are either releasably connected to an instrument body via a cable or are made wireless-communicable. More particularly, the present invention relates to a very useful measuring instrument having measuring electrodes equipped with storage means (memory) in which information regarding the properties of the measuring electrodes is input, or having identification means for identifying the measuring electrodes, provided in the measuring electrodes, and storage means (memory) for identifying the measuring electrodes and storing information regarding the measuring electrodes provided in the instrument body.

For example, in a measuring instrument such as a pH meter or an ion meter releasably connected to an instrument body via a cable, or provided with measuring electrodes made wireless-communicable, it is currently common practice to calibrate the properties of each electrode by using a standard solution before actual use, and to calculate, correct and display a measured value on the basis of the calibration data. For an electrode requiring a correction value as in a conductivity meter or a conductivity cell, it is required to visually read out the correction value displayed on the electrode and set the correction value on the instrument body before use. For electrode control purposes, it is necessary to record the model and the manufacture No. of the electrode.

As described above, therefore, while data calibrated upon use of an electrode or the correction value is stored in the memory, in a conventional measuring instrument, it is necessary, when replacing the electrode with another one, to perform the calibration over again with a standard solution for the new electrode, or set a new correction value.

In some measuring instruments, several calibration values are stored and can be selectively employed. Even in this case, the operator has to remember what part of the stored data corresponds to which of the electrodes so as to select an appropriate electrode by key operation before use. Another problem is that failure to select the correct calibration value means that the measurement will be done on the basis of wrong data. The model and manufacture No. indicated on the electrode label has to be noted down. The instrument body can not automatically identify an electrode.

In an electrode requiring a correction value such as a conductivity cell, a cell constant must be set in the instrument body, as described above. A conductivity cell has electrodes of different shapes, and upon every replacement of an electrode, a cell constant must be set. An accurate measurement can therefore be hindered by an erroneous setting or failure to set correctly. Further, a printout of the result of measurement contains only the result of measurement, without any printed information indicating the electrode for which the result has been obtained.

SUMMARY OF THE INVENTION

The present invention has therefore an object to provide a measuring instrument with a memory or measuring electrodes with a memory, which eliminates the necessity to set a calibration value or a correction value each time an electrode is to be replaced, can automatically identify information such as the model of the electrode or the manufacture No. thereof by means of the instrument body, and permits free selection of an electrode for each use.

Another object of the invention is to provide a measuring instrument with a memory or measuring electrodes with having a memory, which permits electrode control such as a calibration history and the status of the service of electrodes.

Still another object of the invention is to provide a measuring instrument with a memory or measuring electrodes with a memory, which permits avoidance of an erroneous setting or failure to set and the easy replacement of electrodes.

The aforementioned objects are achieved by a measuring instrument with a memory or measuring electrodes each having a memory concernig the invention. In summary, according to one aspect of the present invention, there is provided a measuring instrument having an instrument body and a measuring electrode releasably connected to said instrument body, which comprises storage means provided for storing information regarding the measuring electrode in the measuring electrode, or in a cable or a connector for connecting the measuring electrode to the instrument body.

In an embodiment of the invention, the storage means is an EEPROM, a flash memory, an RAM with a cell backup, an EPROM or a one-time ROM.

In another embodiment of the invention, the instrument body has a read/write means of information into the storage means of the measuring electrode.

In still another embodiment of the invention, the information of the measuring electrode includes information for identifying the measuring electrode.

In still another embodiment of the invention, the information for identifying the measuring electrode includes the model name or the manufacture No.

In still another embodiment of the invention, the information regarding the measuring electrode includes at least one of the following pieces of information such as calibration data, service time, deterioration of the electrode, and the calibration history of the measuring electrode.

According to another aspect of the present invention, there is provided a measuring instrument having an instrument body and measuring electrodes, which comprises identification means provided for identifying the measuring electrodes in the measuring electrodes, or in a cable or a connector for connecting the measuring electrodes to the instrument body; and storage means which recognizes the identification means of the measuring electrodes and stores information regarding the measuring electrodes, provided in the instrument body.

In an embodiment of the invention, the identification means is the physical amount or status changing means such as a switch, an analog switch, a resistor, or a capacitor; a voltage generator, a current generator or generating means of physical amounts including a light; storage means such as an EEPROM, a flash memory, an RAM with a cell backup, an EPROM or a one-time ROM; or bar code means; and the storage means is an EEPROM, a flash memory, an RAM with a cell backup, an EPROM or a one-time ROM.

In another embodiment of the invention, the instrument body has read/write means of information to the identification means of the one or more measuring electrodes.

In still another embodiment of the invention, the information for identifying the measuring electrodes includes the model name or the manufacture No., and the information regarding the measuring electrodes includes at least one piece of information such as calibration data, service time, deterioration of the electrodes, or calibration history of the measuring electrode.

In the measuring instrument of the present invention, the measuring electrode is a pH electrode, an ion electrode, a conductivity cell, a resistance temperature measuring electrode, or a dissolved oxygen electrode.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

The measuring instrument with a memory or measuring electrodes each having a memory of the present invention will now be described further in detail with reference to the drawings. In the following description of embodiments, a pH meter provided with pH electrodes will chiefly be taken up. It is however needless to mention that the invention is applicable also to various other measuring instruments such as those having ion electrodes, conductivity cells, resistance temperature measuring electrodes, or dissolved oxygen electrodes.

Embodiment 1

Figure 1:
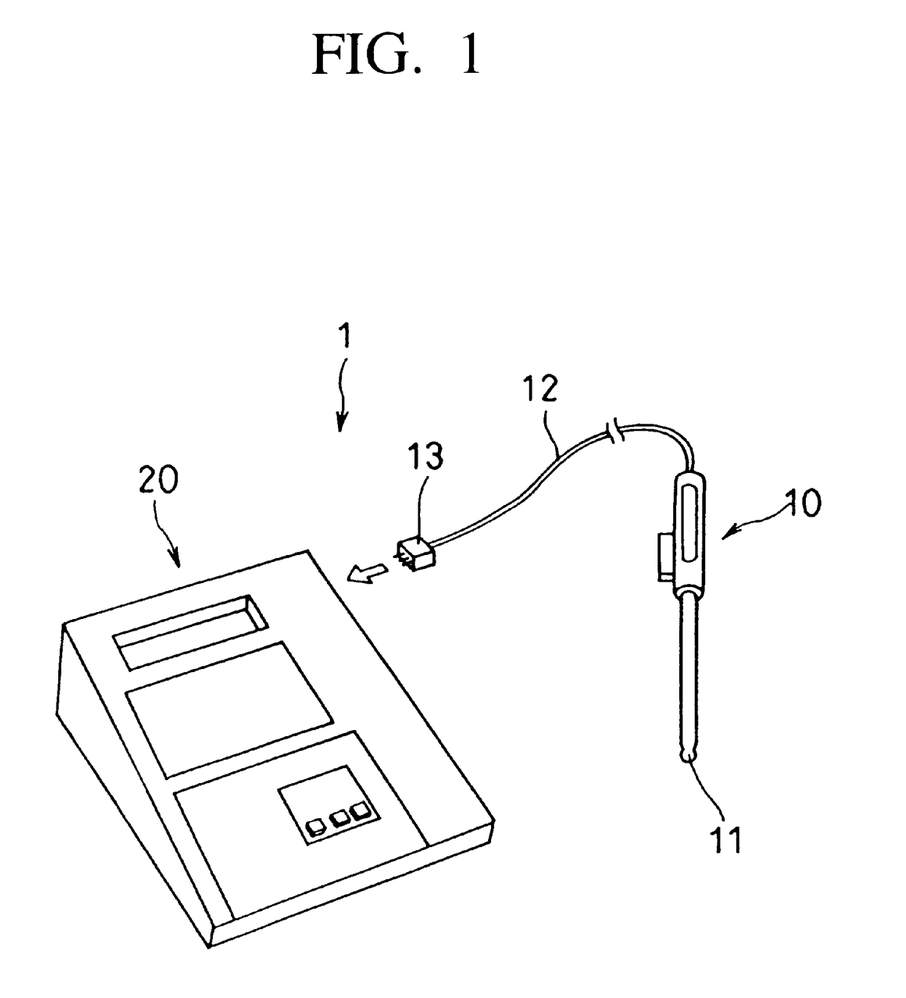
FIG. 1 is a perspective view illustrating the entire configuration of the measuring instrument of the present invention.

FIG. 1 illustrates a pH meter 1 which is an embodiment of the measuring instrument of the invention. The pH meter 1 comprises a pH measuring electrode 10, having a long and slender shape as a whole, provided with a pH sensing section 11 such as a glass sensing membrane at the tip thereof, and an instrument body 20 processing a signal from the pH measuring electrode 10 and displaying the result of such processing. In this embodiment, the measuring electrode 10 is releasably connected to the instrument body 20 with a connector 13 via a cable 12. It is needless to mention that the measuring electrode 10 may be wireless-communicable with the instrument body 20.

Figure 2:
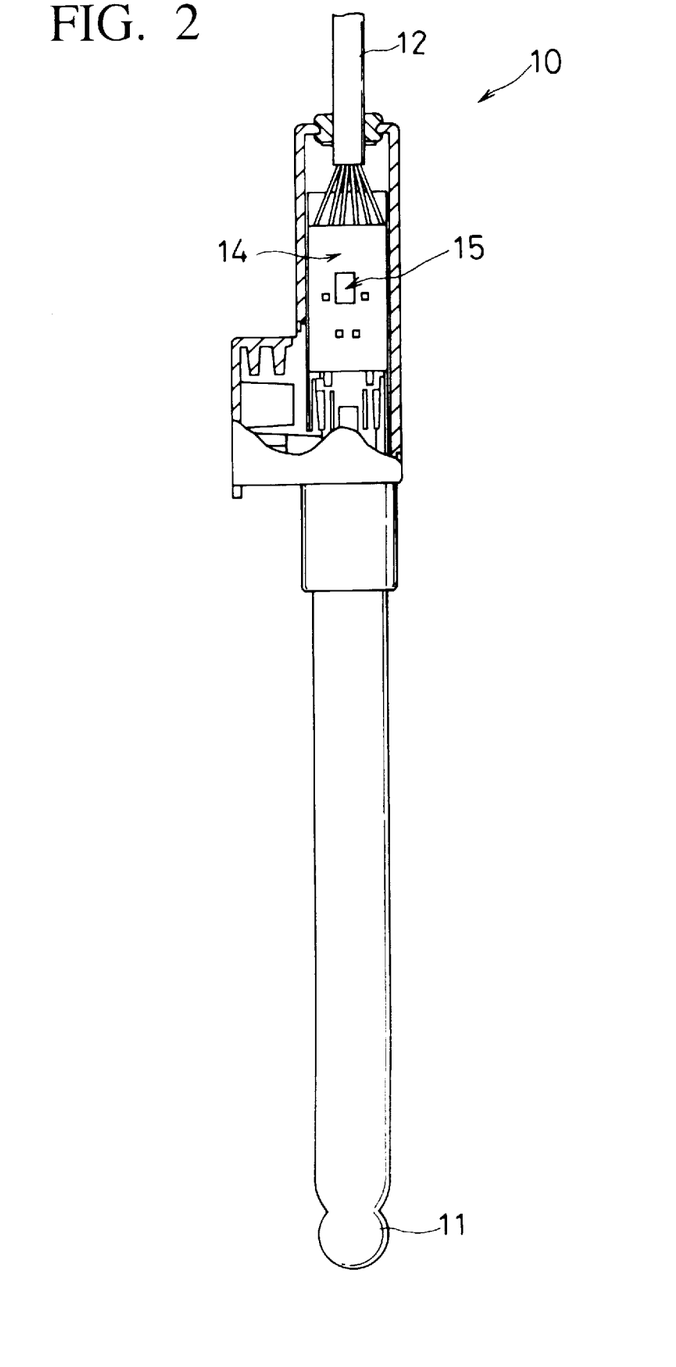
FIG. 2 is a partially cutaway sectional view of the measuring electrode of the measuring instrument of the invention.
Figure 3:
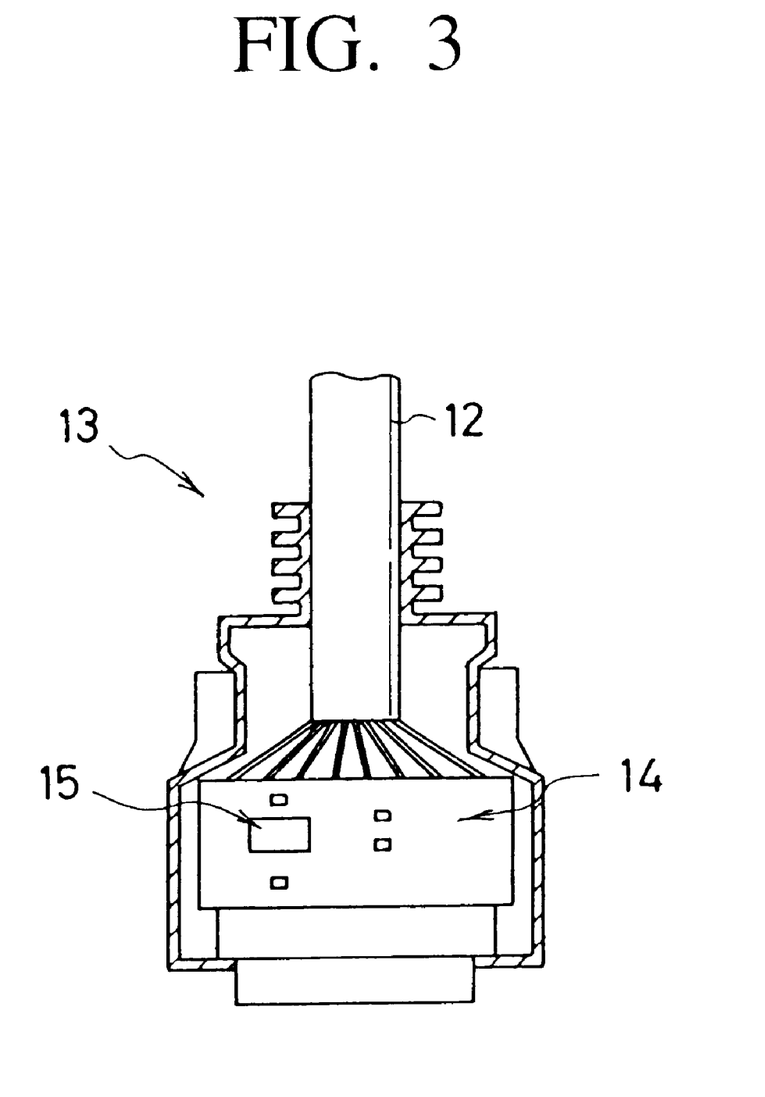
FIG. 3 is a sectional view of the connector section of the measuring instrument of the invention.

According to the invention, as shown in FIG. 2, a printed board 14 is arranged adjacent to an end of the measuring electrode 10, opposite to the pH sensing section 11, where storage means (memory) 15 for storing the data needed by the measuring electrode 10 is attached. As an alternative, the storage means 15 may be positioned on the printed board 14 in the connector 13 attached to the tip of the cable 12 for connecting the measuring electrode 10 to the instrument body 20, as shown in FIG. 3.

In this embodiment, an EEPROM (Electrically Erasable Programmable Read-Only Memory) is used as the storage means 15 of the electrode. Other applicable storage means 15 include storage means such as a flash memory, an RAM with a cell backup, an EPROM and a one-time ROM.

As described above, in a measuring instrument 1 such as a pH meter having the measuring electrode 10, it is necessary to calibrate properties of the electrode by the use of a standard solution before use, and to display the measured value calculated and corrected on the basis of the result of calibration.

Therefore, for example, the model name of the electrode and the manufacture No. thereof are entered upon manufacture of the electrode, and the calibration data, upon inspection, is written into the storage means 15 provided in the electrode 10 as information (data) of the electrode. Further, service time data of the electrode 10 or deterioration data of the electrode 10 may be included as information to be stored in the memory 15.

According to the present invention, in the instrument body 20, there are provided means for reading and storing the information stored in the memory 15 of the aforementioned measuring electrode 10, and means for writing new calibration data into the memory 15 of the measuring electrode 10.

Figure 4:
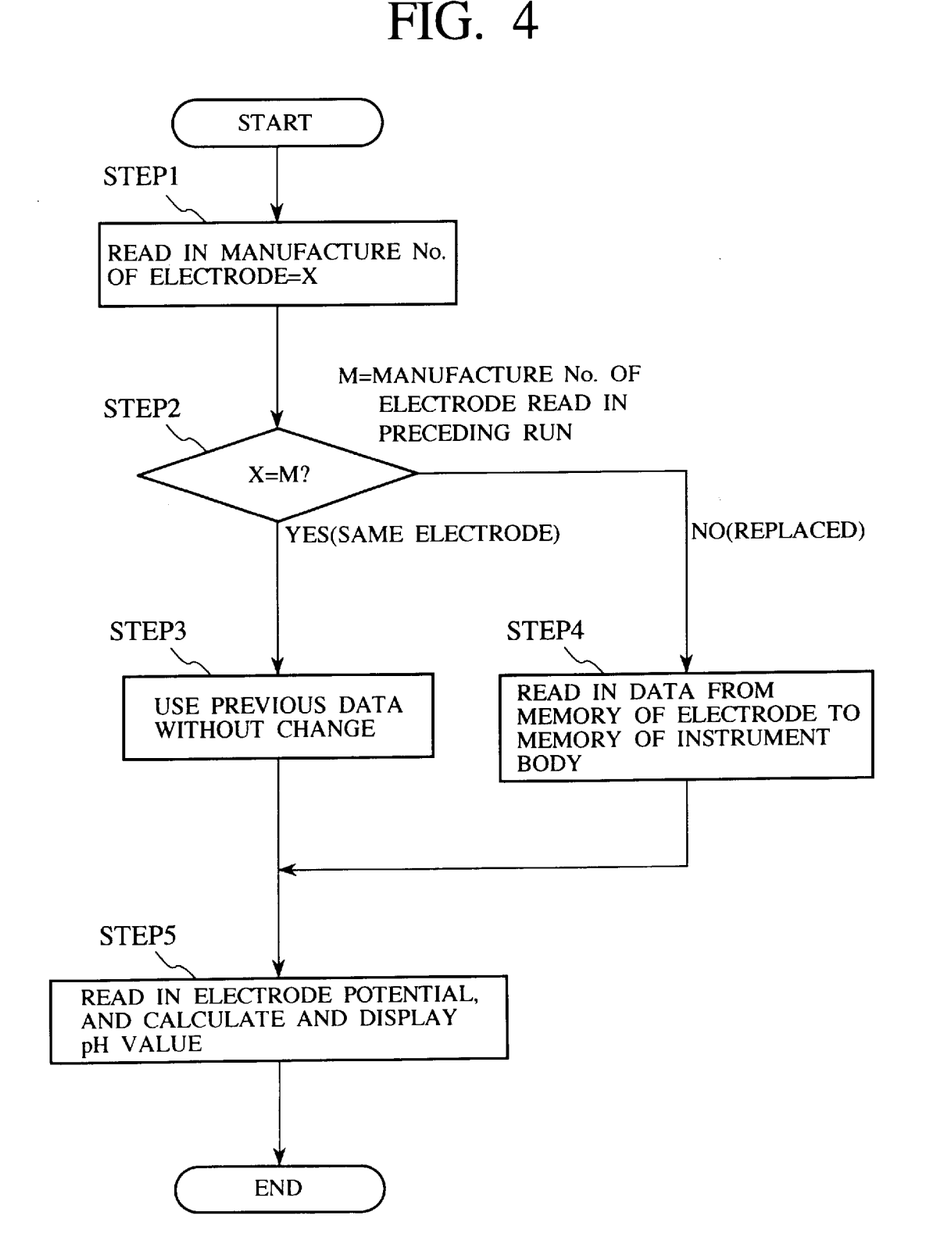
FIG. 4 is a flowchart illustrating the steps of operations upon measurement.

Operations of the measuring instrument having the above-mentioned configuration according to the invention will now be described with reference to FIG. 4.

For measurement with the pH meter, the connector 13 of the measuring electrode 10 is connected to the instrument body 20, and the power supply is turned on to start the measuring mode. The instrument body 20 first reads the model name of the electrode 10, the manufacture No. thereof and the like from the memory 15 of the connected electrode 10 by means of the read/write means provided in the instrument body 20 (Step 1), and determines whether or not the electrode (X) is the one (M) used in the previous run (Step 2). When the electrode (M) is used in succession, the data from the previous run is used as it is (Step 3). When the electrode (X) is determined to be different from the previous one (M), and the calibration data is read out from the memory 15 of the electrode (X) to store the data in the memory of the instrument body 20 (Step 4).

On the basis of the read-in calibration data and the potential resulting from the measuring electrode 10, the instrument body 20 calculates and corrects the pH value, and displays the value as a measured pH value (Step 5). A measuring instrument having a printer can print out data as required.

According to the invention, as described above, the instrument body 20 identifies the model name of the connected electrode 10 and the manufacture No. of the electrode by using data individually stored in different electrodes as connected to the measuring body 20, and carries out the replacement of the data stored in the instrument body 20.

Figure 5:
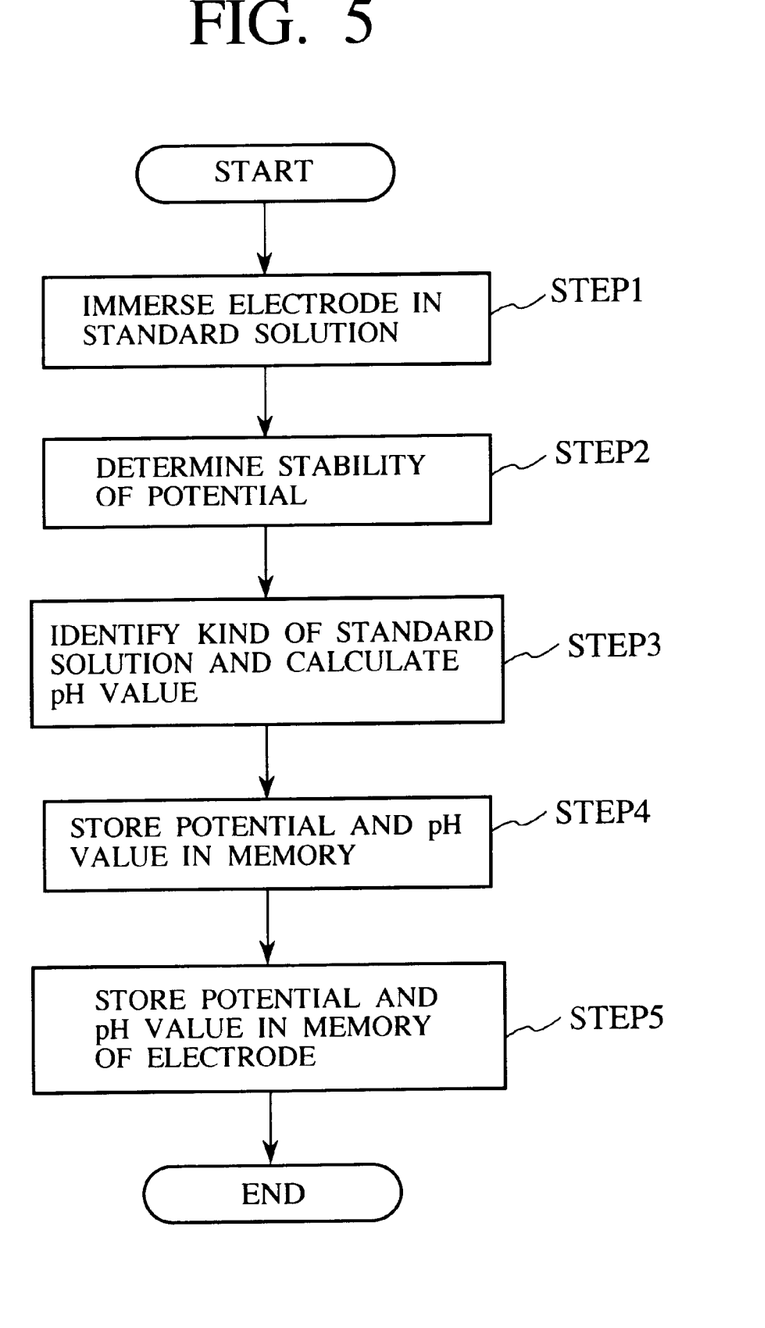
FIG. 5 is a flowchart illustrating the steps of operation upon calibration.

The calibration procedure conducted as required by the use of a standard solution of the electrode for pH measurement will now be described with reference to FIG. 5.

The power supply is turned on to start the calibration mode. The electrode 10 connected to the instrument body 20 is immersed in the standard solution (Step 1). Applicable pH standard solutions include an oxalate pH standard solution (pH 1.68/at 25° C.), a phthalate pH standard solution (pH 4.01/at 25° C.), a neutral phosphate pH standard solution (pH 6.86/at 25° C.), and a borate pH standard solution (pH 9.18/at 25° C.).

Then, when the measured potential is determined to have been stabilized (Step 2), the pH value of the standard solution is calculated (Step 3). That is, Step 3 comprises immersing the electrode in the standard solution, reading out the generated potential, calculating the temperature compensation, and determining the calculated value.

Because the standard solution has unique temperature properties and the pH value differs with temperature, the pH value of the standard solution is calculated on the basis of the temperature measured by a temperature sensor provided separately from the electrode 10. Then, the measured potential and the known pH value are stored in the memory of the instrument body 20 as calibration data (Step 4), and the instrument body 20 writes the calibration data to the memory 15 of the measuring electrode 10 by the write means (Steps 4 and 5).

Calibration of the measuring electrode 10 can be performed by connecting the electrode 10 to the instrument body 20 as described above, but can also be conducted by preparing special calibration apparatus. In this case, it suffices that the instrument body 20 serves only as a simple display for displaying the measured value.

Embodiment 2

In this embodiment, the case where the present invention is applied to a conductivity meter and a cell (measuring electrode) thereof will be described.

In this embodiment also, as in the first embodiment (Embodiment 1), memory means such as an EEPROM is provided in the cell itself or in a connector to the instrument body. The model name and the manufacture No. are written into the memory upon manufacture, and the cell constant is written into the memory upon inspection.

When this cell is connected to the instrument body, therefore, the instrument body reads out a cell constant of the cell, and stores it in the memory of the instrument body. The Measured value is adjusted by the use of this cell constant, corrected, displayed as measured conductivity, and printed out as required.

In this embodiment as in the first embodiment, as described above, the instrument body monitors the status of the cell. Upon replacement of the cell, a change in the cell constant is performed. When calibrating a conductivity cell with the use of a standard solution, a cell constant is automatically calculated, and the resultant value can be stored in the cell.

In the present invention, as described above, the cell constant is thus automatically set. This eliminates failure to set and erroneous settings.

Embodiment 3

A measuring instrument having a measuring electrode with an effective period of time will now be described. A pH electrode, for example, may require a test by weighing when using it for the purpose of transaction certification. In this case, an effective period is one year for an electrode. With such a measuring instrument, the effective period is previously written in the memory of the electrode by the write function of the instrument body upon starting use of the electrode. The instrument body, upon each use of the electrode, reads out the effective period stored in the memory of the electrode, compares the read-out effective period with a clock built in the instrument body, and can display to notify the operator that the end of the period is about to be reached. When the period has elapsed, the instrument body can warn the operator or discontinue service.

As required, the operator can set the effective period to begin upon calibration of the instrument. More specifically, when calibrating the electrode, the operator can write the date and time of the standard solution calibration in the measuring electrode with the use of the write function of the instrument body, compare the calibration date and time of the electrode and the effective period, and cause a message such as a note or a warning to be displayed at regular intervals.

It is also possible to store the service life, of the electrode. That is, the service life is calculated by summing up the periods of time during which the electrode is connected to the instrument body with the power supply of the instrument body turned on. According to the invention, it is possible to differentiate between different electrodes, and hence determine individual sums even when replacing the electrodes.

Further, deterioration determining information of the electrode can also be stored in the memory of the electrode. That is, the electrodes have respective theoretical generated potentials,. Because the individual electrodes are different from each other, calibration is required. Basically, however, a potential far from the theory is never generated. A value lower than the theoretical potential by more than 10%, for example, can therefore be deemed to represent a deterioration.

For example, asymmetric potential and sensitivity are calculated through two-point calibration of the pH meter. An asymmetric potential of over ±30 mV from a standard of 0 mV may be considered to be abnormal, and a sensitivity lower by more than 10% from a standard of 59.16 mV can be deemed to be abnormal (deterioration).

According to the measuring instrument of The invention, as described above, the effective period or the date of calibration, and further, the service life and deterioration information of each electrode are stored in the electrode. This permits very easy achievement of electrode control.

While the above description has covered the pH meter, the present invention is similarly applicable also to an ion meter, a conductivity meter and a dissolved oxygen meter with the same advantages.

Embodiment 4

In the case of a measuring instrument using an ionic selection electrode where calibration is carried out with an ion standard solution, the resultant data of calibration is written and stored in the memory of the electrode. The date and time of calibration is also written together with the calibration data. In the case of an ion electrode, the kind of ion derived from the read-out model name of the electrode can also be displayed or printed out, together with the result of measurement, since various types of ion electrode are available. Several kinds of ion electrode can therefore be used without the necessity of a particular switching operation for the instrument body. It is needless to mention that, the calibration period can be controlled on the basis of the data stored in the electrode in the same manner as in the aforementioned embodiments.

Embodiment 5

In a measuring instrument such as a thermistor thermometer, the addition of correction resistance to a thermistor for a measuring electrode so as to increase the precision of temperature measurement or interchangeability, or selective use of the elements having the same characteristics is carried out. Therefore, according to the present invention, the memory means is disposed in the thermistor electrode, or a cable or connector to write the characteristic data of the thermistor such as B constant and a nominal resistant value. The reading of the data upon connection and the calculation using the measuring resistance value makes it possible to carry out the measurement with high accuracy.

This embodiment can be applied to other measuring instruments using a resistance temperature measuring electrode such as a platinum resistance or the like, in place of the thermistor electrode, and can attain the same advantages.

Embodiment 6

Figure 6:
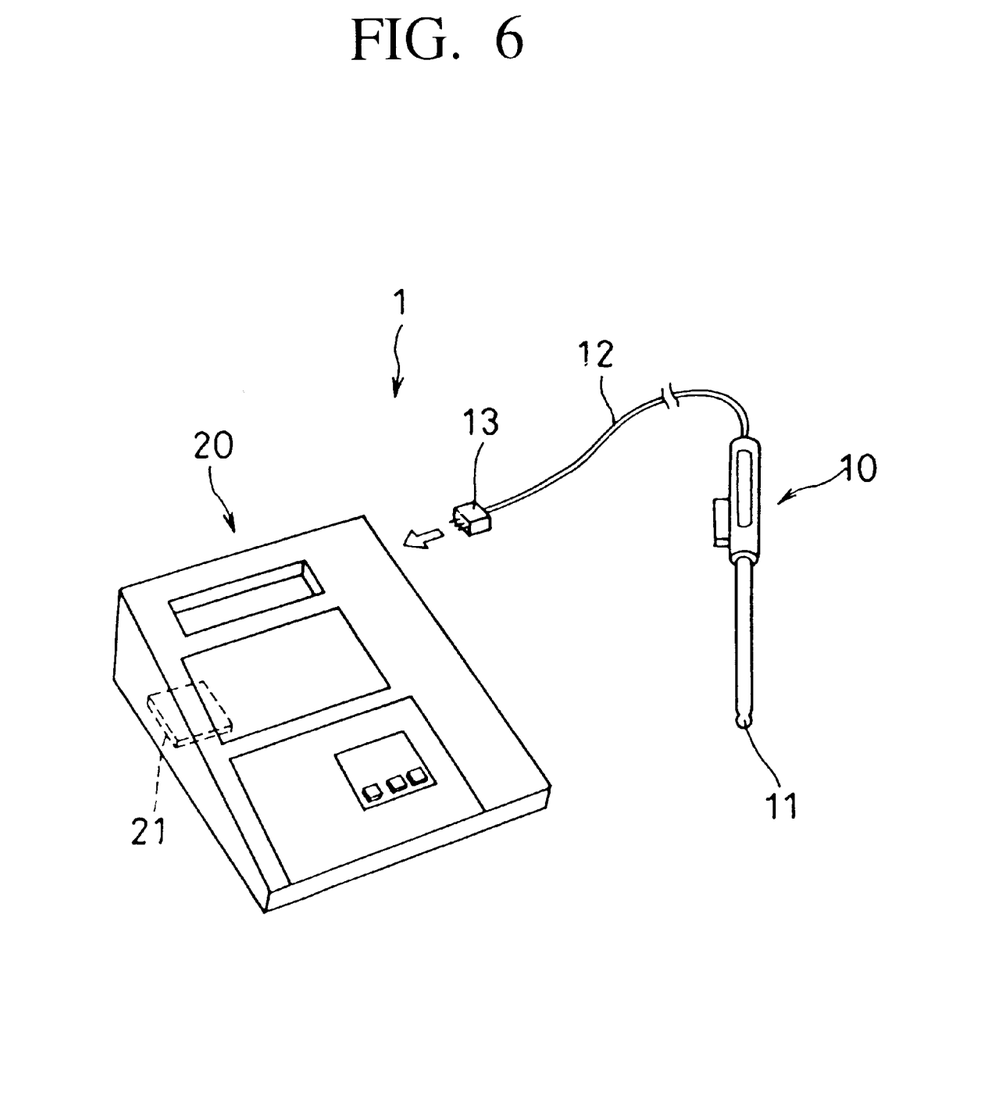
FIG. 6 is a perspective view illustrating the entire configuration of the measuring instrument of the present invention.

FIG. 6 illustrates a pH meter 1 which is still another embodiment of the measuring instrument of the invention. The pH meter 1 comprises a pH measuring electrode 10, having a long and slender shape as a whole, provided with a pH sensing section 11 such as a glass sensing membrane at the tip thereof, and an instrument body 20 processing a signal from the pH measuring electrode 10 and displaying the result of such processing. In this embodiment, the measuring electrode 10 is releasably connected to the instrument body 20 with a connector 13 via a cable 12. It is needless to mention that the measuring electrode 10 may be wireless-communicable with the instrument body 20.

Figure 7:
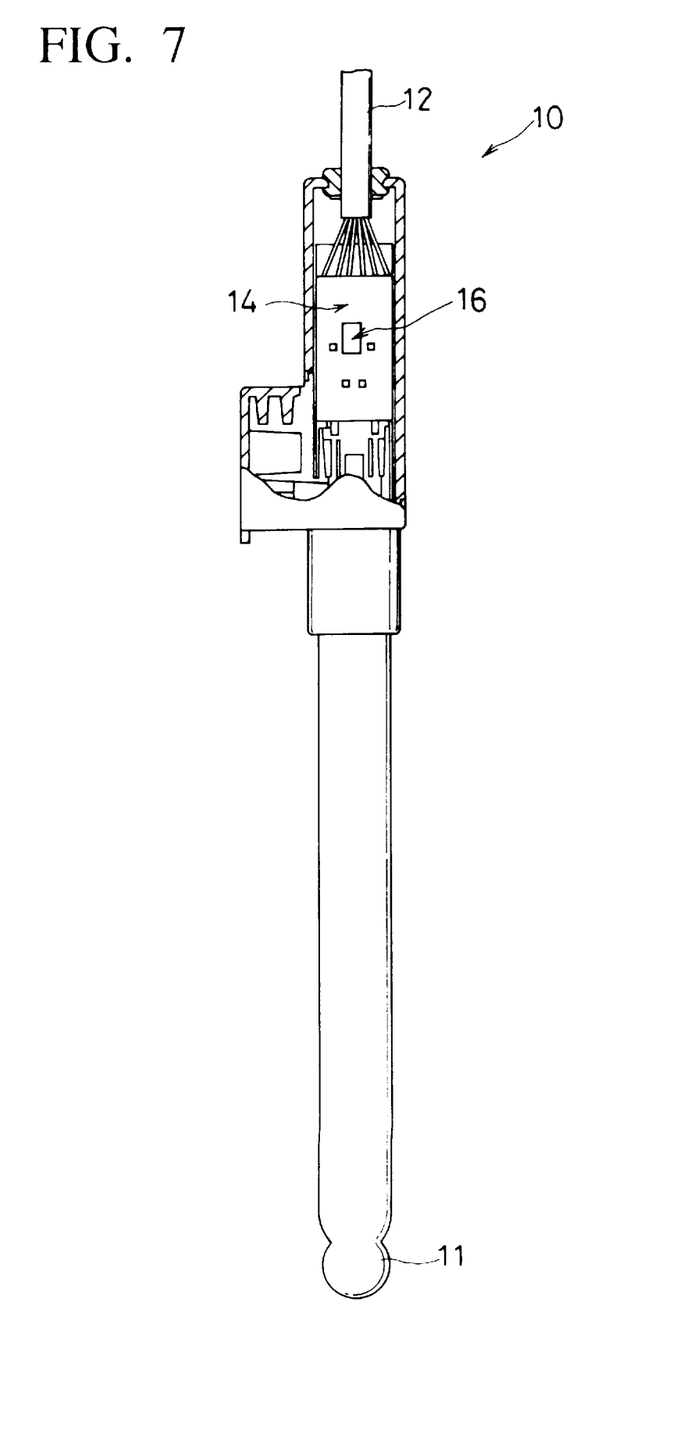
FIG. 7 is a partially cutaway sectional view of the measuring electrode of the measuring instrument of the invention.
Figure 8:
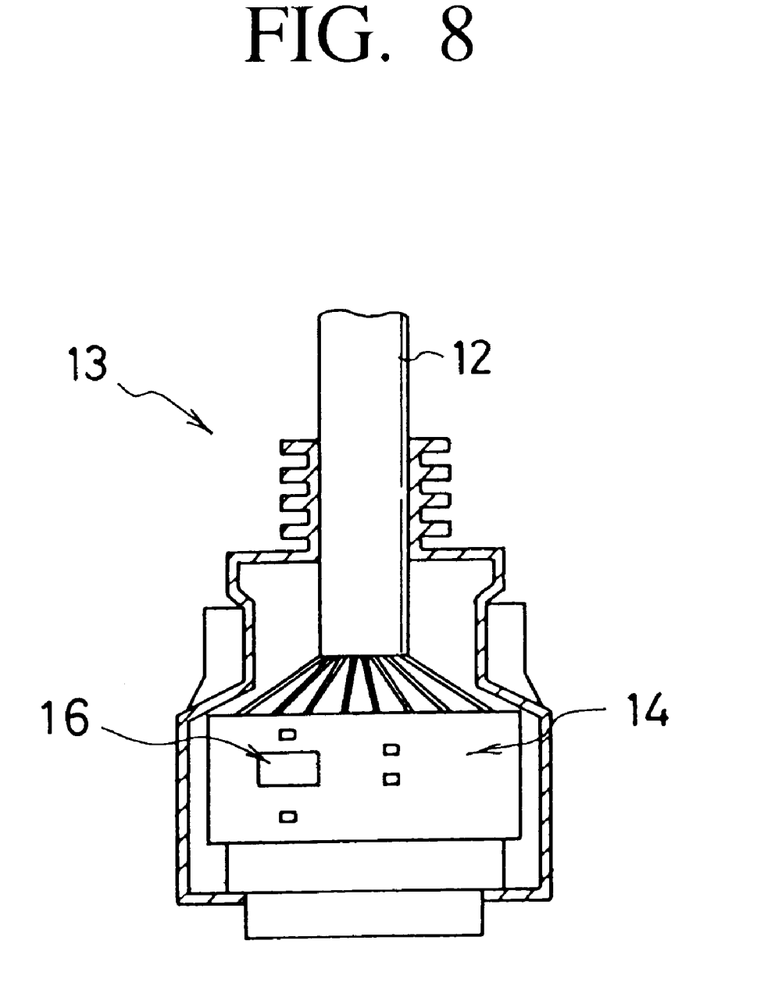
FIG. 8 is a sectional view of the connector section of the measuring instrument of the invention.

According to the invention, as shown in FIG. 7, a printed board 14 is arranged adjacent to an end of the measuring electrode 10, opposite to the pH sensing section 11, where identification means 16 for identifying the measuring electrode 10 is attached. As an alternative, the identification means 16 may be provided on the printed board 14 in the connector 13 attached to the tip of the cable 12 for connecting the measuring electrode 10 to the instrument body 20, as shown in FIG. 8.

In this embodiment, an EEPROM (Electrically Erasable Programmable Read-Only Memory) is used as the identification means 16 of the electrode. Other applicable identification means 16 includes storage means such as a flash memory, an RAM with a cell backup, an EPROM and a one-time ROM; changing means for the physical amount or status such as a switch, an analog switch, a resistor, and a capacitor; a voltage generator, a current generator or generating means of a physical amount such as a light; and bar code means. The kind of electrode 10, the model name thereof, the manufacture No. thereof and the like are previously written in the identification means 16.

According to the invention, the instrument body 20 is provided with storage means (memory) 21 for recognizing the identification means 16 of the measuring electrode 10 and recording information regarding the measuring electrode 10. Applicable storage means 21 include an EEPROM, a flash memory, an RAM with a cell backup, an EPROM and a one-time ROM.

As described above, in a measuring instrument 1 such as a pH meter having the measuring electrode 10, it is necessary to calibrate properties of the electrode by the use of a standard solution before use, and display the measured value on the basis of the result of calibration.

Therefore, for example, the kind of the electrode, the model name thereof, and the manufacture No. thereof are entered as information for identifying the electrode upon manufacture of the electrode, into the identification means 16 provided in the electrode 10.

In the memory 21 of the instrument body 20, when the measuring electrode 10 is first connected to the instrument body 20 to inspect the measuring electrode 10, calibration data to be executed upon inspection is read in and stored in an area corresponding to the identification No. of the electrode as information (data) of the measuring electrode 10. Further, service time data of the electrode 10 or deterioration data of the electrode 10 may be included in the information to be stored in the memory 21.

In the instrument body 20, therefore, there are provided means for reading identification information of the identification means 16 of the aforementioned measuring electrode 10 and for writing the information into the memory 21, and means for writing new calibration data upon inspection of the measuring electrode 10 into the memory 21. When another measuring electrode 10 is connected to the instrument body 20, the identification information of the identification means 16 of the new electrode is read in. The kind of electrode is identified, and the calibration data of this electrode is differentiated from the data of the other electrodes, thereby individually recording the data into the memory 21.

According to the invention, as described above, even when a plurality of measuring electrodes are used by connecting to a single instrument body 20, pieces of information including calibration data, service time data and electrode deterioration data are stored in the memory 21 at areas corresponding to the plurality of electrodes 10, in the instrument body 20. Upon connection of the measuring electrode 10 to the instrument body 20, the measuring electrodes are automatically recognized, thus eliminating the necessity for the operator to determine the kind of electrode 10 and to select calibration data for use.

Figure 9:
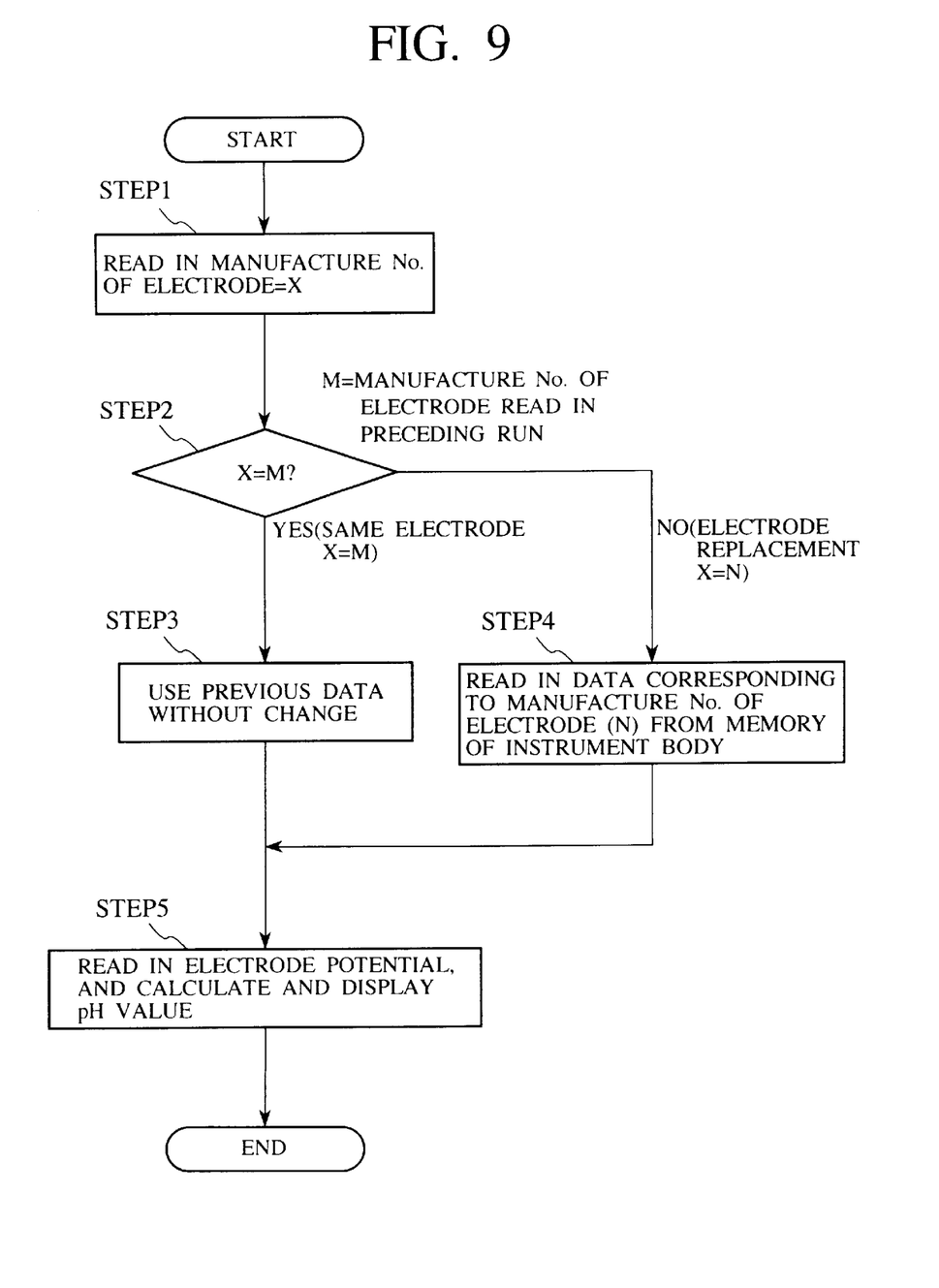
FIG. 9 is a flowchart illustrating the steps of operation upon measurement.

Operations of the measuring instrument having the above-mentioned configuration according to the invention will now be described with reference to FIG. 9.

For measurement with the pH meter, the connector 13 of the measuring electrode 10 is connected to the instrument body 20, and the power supply is tuned on to start the measuring mode. The instrument body 20 first reads in the model name of the electrode 10, the manufacture No. thereof and the like from the identification means 16 of the connected electrode 10 by means of the read/write means provided in the instrument body 20 (Step 1), and identifies the electrode 10 to determine whether or not the electrode (X) is the one (M) used in the previous run, i.e., whether or not the electrode (X) has been replaced (Step 2). When the electrode (M) is used in succession, the data for the previous run is used as it is (Step 3).

When the electrode (X) is an electrode (N) different from the one (M) used for the previous measurement, i.e., when the electrode has been replaced, the electrode is determined to be different from the previous one (M), and the calibration data for this electrode (N) is read out from the memory 21 of the instrument body 20 (Step 4).

On the basis of the read-in calibration data and the potential resulting from the measuring electrode 10, the instrument body 20 calculates and corrects the pH value, and displays it as a measured pH value (Step 5). A measuring instrument having a printer can print out data as required.

According to the invention, as described above, the instrument body 20 identifies the connected electrode 10, and carries out measurement using data, stored in the memory 21 of the instrument body, corresponding to that electrode 10.

Figure 10:
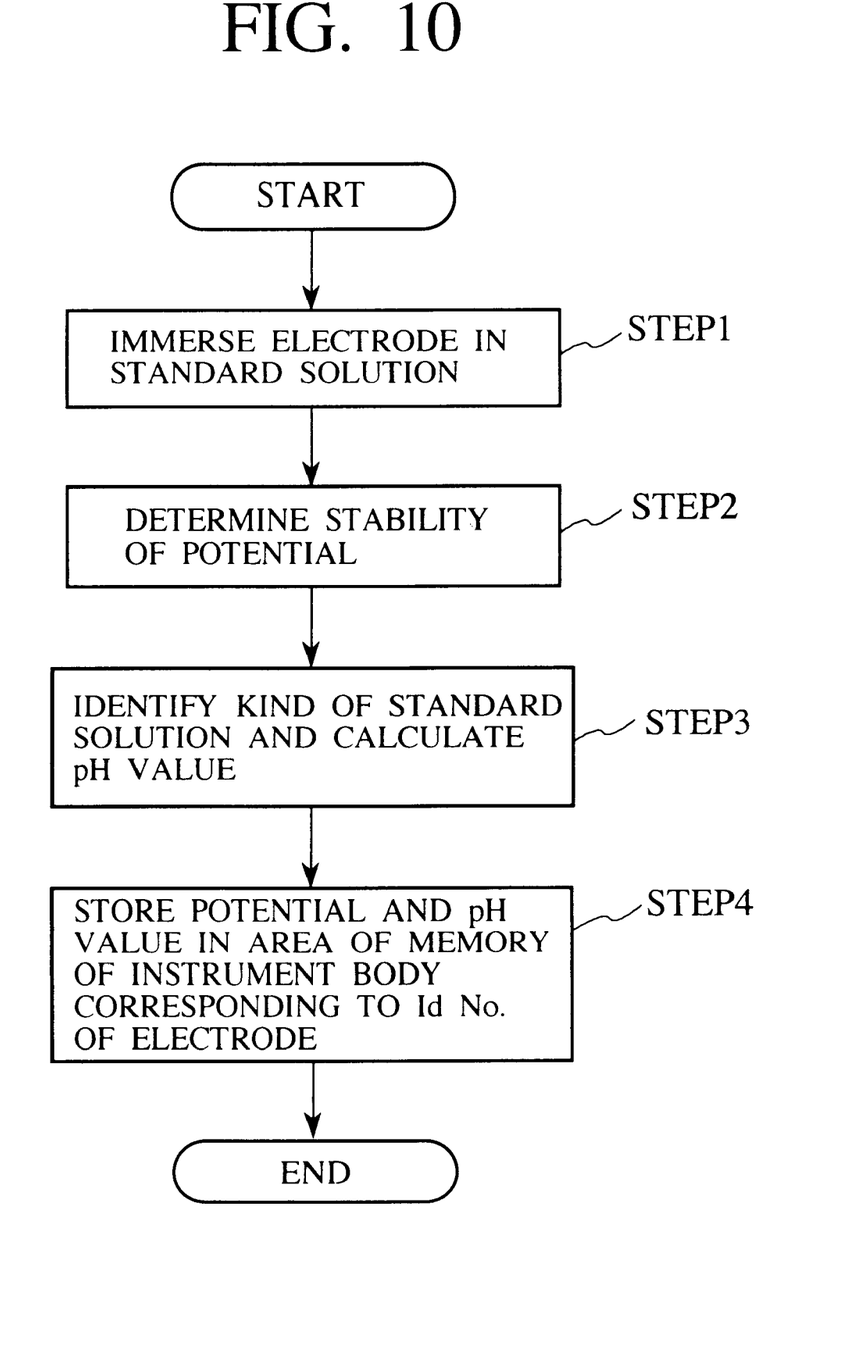
FIG. 10 is a flowchart illustrating the steps of operation upon calibration.

The calibration procedure conducted as required by the use of a standard solution of the electrode for pH measurement will now be described with reference to FIG. 10.

The power supply is turned on to start the calibration mode. The electrode 10 connected to the instrument body 20 is immersed in the standard solution (Step 1). Applicable pH standard solutions include an oxalate pH standard solution (pH 1.68/at 25° C.), a phthalate pH standard solution (pH 4.01/at 25° C.), a neutral phosphate pH standard solution (pH 6.86/at 25° C.), and a borate pH standard solution (pH 9.18/at 25° C.).

Then, when the measured potential is determined to have been stabilized (Step 2), the pH value of the standard solution is calculated (Step 3). That is, Step 3 comprises immersing the electrode in the standard solution, reading out the generated potential, calculating the temperature compensation, and determining the calculated value.

Because a standard solution has unique temperature properties and the pH value differs according to temperature, the pH value of the standard solution is calculated on the basis of the temperature measured by a temperature sensor provided separately from the electrode 10. Then, the measured potential and the known pH value are stored in the memory 21 of the instrument body 20 at a position corresponding to that electrode 10 (Step 4).

Calibration of the measuring electrode 10 can be performed by connecting the electrode 10 to the instrument body 20 as described above, but can also be conducted by preparing a special calibration apparatus. In this case, it suffices that the instrument body 20 serves only as a simple display for displaying the measured value.

Embodiment 7

In this embodiment, the case of application of the present invention to a conductivity meter and a cell (measuring electrode) thereof will be described.

In this embodiment also, as in Embodiment 6, identification means 16 such as a resistor is provided in the cell itself which is a measuring electrode 10, or in a connector 13 to the instrument body 20. By using one or more such resistors 16, it is possible to identify the model name and the manufacture No. from the individual resistance values.

A memory such as an RAM with a cell backup as shown in Embodiment 6 may be used as storage means 21 for storing information regarding the cell 10 in the instrument body 20.

When this cell 10 is connected to the instrument body 20, therefore, the instrument body 20 reads out the resistance value of one or more resistors 16 provided in the cell 10, and identifies the model name and the manufacture No. of the cell. A cell constant corresponding to the cell 10 is stored in the instrument body 20. The measured value is adjusted by the use of this cell constant, corrected, displayed as a measured conductivity, and printed out as required.

In this embodiment as in Embodiment 6, as described above, the instrument body 20 monitors the status of the cell 10. Upon replacement of the cell 10, a cell constant corresponding to the new cell 10 after replacement is manually entered, and the cell constant is stored in an area of the memory 21 of the instrument body 20 corresponding to the identification No. of the cell. As a result, when using a once identified cell 10 as a replacement, the cell constant written in as data in the memory 21 is automatically read out and employed.

When calibrating a conductivity cell 10 with the use of a standard solution, a cell constant is automatically calculated, and the resultant value can be stored in an area of the memory 21 of the instrument body 20 corresponding to the identification No. of the cell.

In the present invention, as described above, when the cell constant is once stored in the memory 21 of the instrument body 20 by identifying the cell 10, the cell 10 is automatically identified thereafter. The cell constant is thus automatically read out. This not only eliminates the necessity to enter the cell constant again, but also makes it possible to reduce the risk of an input error of the cell constant, thus permitting measurement with a high reliability.

Embodiment 8

A measuring instrument having a measuring electrode 10 with an effective period of time will now be described. A pH electrode, for example, may require a test by weighing when using it for the purpose of transaction certification. In this case, the effective period is for a year for an electrode 10. In such a measuring instrument, the effective period is previously written in an area corresponding to the identification No. of the electrode in the memory 21 of the instrument body upon starting use of the electrode 10. The instrument body 20 identifies the electrode 10 upon each use of the electrode 10, reads out the effective time period corresponding to the electrode 10 from the memory 21 of the instrument body 20, compares the read-out effective time period with a clock built in the instrument body 20, and can thus notify when the end of the period is about to be reached. When the period has elapsed, the instrument body 20 warns the operator, or can discontinue service.

As required, the operator can set the effective period to begin upon calibration of the instrument. More specifically, when calibrating the electrode 10, the operator can write the date and time of standard solution calibration in an area of the memory 21 of the instrument body 20 corresponding to the identification No. of the measuring electrode 10 by the use of the write function of the instrument body 20, compare the calibration date of the electrode and the effective time period, and cause a message such as a note or a warning to be displayed at regular intervals.

It is also possible to store the service life or the electrode in an area corresponding to the identification No. of the electrode 10. That is, the service life is calculated by summing up periods during which the electrode 10 is connected to the instrument body 20 with the power supply of the instrument body turned on. According to the invention, it is possible to discriminate between different electrodes 10, and hence to determine individual sums even when replacing the electrodes 10.

Further, deterioration determining information of the electrode 10 can also be stored in an area of the memory 21 of the instrument body 20 corresponding to the identification No. of the electrode 10. That is, the electrodes 10 have respective theoretical generated potentials. Because the individual electrodes 10 are different from each other, calibration is required. Basically, however, a potential far from the theory is never generated. A value lower than the theoretical potential by more than 10%, for example, can therefore be deemed to represent a deterioration.

For example, an asymmetric potential and a sensitivity are calculated through two-point calibration of the pH meter. An asymmetric potential of over ±30 mV from a standard of 0 mV may be considered to be abnormal, and a sensitivity lower by more than 10% from a standard of 59.16 mV can be deemed to be abnormal (deterioration).

According to the measuring instrument of the invention, as described above, the effective period or the date of calibration, and further, the service life and deterioration information of each electrode are stored in an area of the memory 21 of the instrument body corresponding to the identification No. of the electrode 10. This permits very easy achievement of electrode 10 control.

While the above description has covered the pH meter, the present invention is similarly applicable also to an ion meter, a conductivity meter and a dissolved oxygen meter with the same advantages.

Embodiment 9

In the case of a measuring instrument using an ionic selection electrode and calibration is carried out with an ion standard solution, the resulting calibration data is written and stored in an area of the memory of the instrument body 20 corresponding to the identification No. of the electrode. The date of calibration is also written together with the calibration data. In the case of an ion electrode, the kind of ion derived from the read-out model name of the electrode 10 can also be displayed or printed out, together with the result of measurement, since various types of ion electrode are available. Several kinds of ion electrode can therefore be used without the necessity for a particular switching operation of the instrument body 20. It is needless to mention that, because a calibration period can be stored in an area of the memory 21 of the instrument body 20 corresponding to the electrode, it is possible to carry out control on the basis thereof in the same manner as in the aforementioned embodiments.

As described above, the measuring instrument of the present invention has an instrument body and a measuring electrode releasably connected to the instrument body, in which storage means for storing information regarding the measuring electrode is provided in the measuring electrode, or in a cable or a connector for connecting the measuring electrode to the instrument body. Alternatively, the measuring instrument with a memory of the present invention has an instrument body and a measuring electrode and has a configuration in which identification means for identifying the measuring electrode is provided in the measuring electrode or in a cable or a connector for connecting the measuring electrode to the instrument body, and storage means for recognizing the identification means of the measuring electrode and recording information regarding the measuring electrode is provided in the instrument body. The following advantages are therefore available:

(1) It is not necessary to set a calibration or correction value at each replacement of the electrode, an appropriate electrode suitable for a particular use can be selected.

(2) It is possible and easy to carry out electrode control over the calibration history and status of use of the electrode.

(3) It is possible to avoid the risk of an erroneous setting or failure to make a setting, and the electrode can easily be replaced.

What is claimed is:

1. A pH measuring instrument comprising:

an instrument body including read/write means;

a cable;

a connector for releasably connecting a first end of the cable to the instrument body;

a pH electrode connected to a second end of the cable; and storage means for storing information regarding said pH electrode, the storage means being located within one of the pH electrode, the cable and the connector, the information being transferred between the storage means and the instrument body by the read/write means.

2. A pH measuring instrument according to claim 1, wherein said storage means is one of an EEPROM, a flash memory, a RAM with a cell backup, an EPROM and a one-time ROM.

3. A pH measuring instrument according to claim 1 wherein said information of said pH electrode includes information identifying said pH electrode.

4. A pH measuring instrument according to claim 3, wherein said information for identifying said pH electrode includes one of a model name and a manufacture number.

5. A pH measuring instrument according to claim 1, wherein said information regarding the pH electrode includes at least one of calibration data, service time, deterioration of the electrode, and the calibration history of said pH electrode.

6. A pH measuring instrument comprising:

an instrument body including read/write means, a cable;

a connector for releasably connecting a first end of the cable to the instrument body;

a pH electrode connected to a second end of the cable;

identification means for identifying said pH electrode, the identification means being located within one of the electrode, the cable and the connector; and storage means responsive to the identification means for storing information regarding the identification of said pH electrode, the storage means being located within one of the pH electrode, the cable and the connector, the identification information being transferred between the storage means and the instrument body by the read/write means.

7. A pH measuring instrument according to claim 6, wherein said identification means is one of a switch, an analog switch, a resistor, a capacitor, a voltage generator, a current generator and a generator of physical amounts including light and wherein the storage means is one of an EEPROM, a flash memory, a RAM with a cell backup, an EPROM, a one-time ROM and bar code means.

8. A pH measuring instrument according to claim 6 wherein said storage means is one of an EEPROM, a flash memory, a RAM with a cell backup, an EPROM and a one-time ROM.

9. A pH measuring instrument according to claim 6, wherein said information for identifying said measuring electrode includes one of a model name and a manufacture number.

10. A pH measuring instrument according to claim 6, wherein said information regarding said pH electrode includes at least one of calibration data, service time and electrode deterioration, and the calibration history of said pH electrode.

* * * * *